US00PP31236P2

(12) United States Plant Patent
Misato et al.

(10) Patent No.: US PP31,236 P2
(45) Date of Patent: Dec. 17, 2019

(54) ***MANDEVILLA* PLANT NAMED 'SUNPA 316'**

(50) Latin Name: *Mandevilla hybrida*
Varietal Denomination: Sunpa 316

(71) Applicants: Tomoya Misato, Shiga (JP); Masahiro Yamada, Shiga (JP)

(72) Inventors: Tomoya Misato, Shiga (JP); Masahiro Yamada, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 15/999,922

(22) Filed: Sep. 4, 2018

(51) Int. Cl.
*A01H 5/02* (2018.01)
*A01H 6/08* (2018.01)

(52) U.S. Cl.
USPC ..... Plt./232
CPC ..... *A01H 6/088* (2018.05)

(58) Field of Classification Search
USPC ..... Plt./232
See application file for complete search history.

*Primary Examiner* — Anne Marie Grunberg
(74) *Attorney, Agent, or Firm* — C. A. Whealy

(57) ABSTRACT

A new and distinct cultivar of *Mandevilla* plant named 'Sunpa 316', characterized by its semi-climbing plant habit; vigorous growth habit; freely branching habit; early and freely flowering habit; long flowering period; and medium-sized bright red-colored flowers with yellow orange-colored throats.

1 Drawing Sheet

Botanical designation: *Mandevilla hybrida.*
Cultivar denomination: 'SUNPA 316'.

BACKGROUND OF THE INVENTION

The present invention relates to a new and distinct cultivar of *Mandevilla* plant, botanically known as *Mandevilla hybrida* and hereinafter referred to by the name 'Sunpa 316'.

The new *Mandevilla* plant is a product of a planned breeding program conducted by the Inventor in Higashiomi, Shiga, Japan. The objective of the breeding program is to create new vining and freely branching *Mandevilla* plants with freely flowering habit and attractive flowers.

The new *Mandevilla* plant originated from an open-pollination in Higashiomi, Shiga, Japan in May, 2012 of a proprietary selection of *Mandevilla hybrida* identified as code number 11MB22-3, not patented, as the female, or seed parent with an unknown selection of *Mandevilla hybrida*, as the male, or pollen, parent. The new *Mandevilla* plant was discovered and selected by the Inventor as a single flowering plant from within the progeny of the stated open-pollination in a controlled greenhouse environment in Higashiomi, Shiga, Japan in September, 2013.

Asexual reproduction of the new *Mandevilla* plant by terminal vegetative cuttings in Higashiomi, Shiga, Japan since March, 2014 has shown that the unique features of this new *Mandevilla* plant are stable and reproduced true to type in successive generations.

SUMMARY OF THE INVENTION

Plants of the new *Mandevilla* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Sunpa 316'. These characteristics in combination distinguish 'Sunpa 316' as a new and distinct *Mandevilla* plant:

1. Semi-climbing plant habit.
2. Vigorous growth habit.
3. Freely branching habit.
4. Early and freely flowering habit.
5. Long flowering period.
6. Medium-sized bright red-colored flowers with yellow orange-colored throats.

Plants of the new *Mandevilla* can be compared to plants of the female parent selection. Plants of the new *Mandevilla* differ primarily from plants of the female parent selection in the following characteristics:

1. Plants of the new *Mandevilla* are semi-climbing whereas plants of the female parent selection are climbing.
2. Plants of the new *Mandevilla* and the female parent selection differ in flower color as plants of the new *Mandevilla* have bright red-colored flowers whereas plants of female parent selection have rose pink-colored flowers.

Plants of the new *Mandevilla* can be compared to plants of the *Mandevilla amabilis* X *Mandevilla boliviensis* 'Sunmandecrim', disclosed in U.S. Plant Pat. No. 15,539. In side-by-side comparisons, plants of the new *Mandevilla* differ from plants of 'Sunmandecrim' in the following characteristics:

1. Plants of the new *Mandevilla* have shorter internodes than plants of 'Sunmandecrim'.
2. Leaves of plants of the new *Mandevilla* are darker green in color than leaves of plants of 'Sunmandecrim'.
3. Plants of the new *Mandevilla* and 'Sunmandecrim' differ in flower color as plants of the new *Mandevilla* have bright red-colored flowers whereas plants of 'Sunmandecrim' have dark red-colored flowers.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph at the top of the sheet comprises a side perspective view of a typical flowering plant of 'Sunpa 316' grown in a container.

The photograph at the bottom of the sheet is a close-up view of a typical flowering plant of 'Sunpa 316'.

DETAILED BOTANICAL DESCRIPTION

The aforementioned photographs and following observations, measurements and values describe plants grown during the summer in 15-cm containers in an outdoor nursery in Higashiomi, Shiga, Japan and under cultural practices typical of commercial *Mandevilla* production. During the production of the plants, day temperatures averaged 25° C. and night temperatures averaged 15° C. Plants were six months old when the photographs and detailed description were taken. In the following description, color references are made to The Royal Horticultural Society Colour Chart, 2007 Edition, except where general terms of ordinary dictionary significance are used.

Botanical classification: *Mandevilla hybrida* 'Sunpa 316'.

Parentage:

*Female, or seed, parent*.—Proprietary selection of *Mandevilla hybrida* identified as code number 11MB22-3, not patented.

*Male, or pollen, parent*.—Unknown selection of *Mandevilla hybrida*, not patented.

Propagation:

*Type*.—By terminal vegetative cuttings.

*Time to initiate roots, summer and winter*.—About two weeks at temperatures about 23° C. to 25° C.

*Time to produce a rooted young plant, summer and winter*.—About five to six weeks at temperatures about 23° C. to 25° C.

*Root description*.—Fibrous; typically light brown in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Semi-climbing plant habit; vigorous growth habit; freely branching habit.

*Plant height* (*with support*).—About 134 cm.

*Lateral branch description*.—Length: About 10 cm. Diameter: About 2.4 mm. Internode length: About 3.5 cm. Strength: Strong, flexible. Texture: Smooth, glabrous. Color, developing: Close to 144A; slightly tinged with close to N172D. Color, fully developed: Close to 199A.

Leaf description:

*Arrangement*.—Opposite, simple.

*Length*.—About 6.5 cm.

*Width*.—About 3.8 cm.

*Shape*.—Elliptic.

*Apex*.—Acuminate.

*Base*.—Rounded.

*Margin*.—Entire.

*Texture and luster, upper and lower surfaces*.—Densely pubescent; moderately glossy.

*Venation pattern*.—Pinnate, reticulate.

*Color*.—Developing leaves, upper surface: Close to between 143A and 144A. Developing leaves, lower surface: Close to 147B to 147C. Fully expanded leaves, upper surface: Close to NN137A; venation, close to 143C. Fully expanded leaves, lower surface: Close to 147B; venation, close to 144D.

*Petioles*.—Length: About 1.4 cm. Diameter: About 1.6 mm. Texture, upper and lower surfaces: Smooth, glabrous. Color, upper and lower surfaces: Close to 144A.

Flower description:

*Flower type and habit*.—Single salverform flowers arranged in axillary racemes; flowers face mostly upright to outwardly; freely flowering habit with about four to six flowers per inflorescence and about 55 flowers developing per plant.

*Natural flowering season*.—Early flowering habit, plants begin flowering about six weeks after planting; long flowering period, plants flower continuously from early summer until late autumn in Japan.

*Flower longevity on the plant*.—About seven to ten days; flowers not persistent.

*Fragrance*.—None detected.

*Flower buds*.—Height: About 6.3 cm. Diameter: About 1.1 cm. Shape: Rhombic. Color: Distally, close to 53B; mid-section, close to 145C; proximally, close to 145B tinged with close to N34A.

*Flowers*.—Appearance: Salverform; flared trumpet, corolla fused and five-parted; flowers roughly star-shaped. Diameter: About 7 cm. Depth (length): About 6.4 cm. Throat diameter: About 1.7 cm. Tube length: About 2.2 cm. Tube diameter, proximally: About 3.1 mm.

*Corolla*.—Quantity and arrangement: Five petals arranged in a single whorl and fused towards the base into an elongated tube; petal lobes slightly imbricate. Petal lobe length: About 2.9 cm. Petal lobe width: About 2.5 cm. Petal lobe shape: Obovate, moderately asymmetrical. Petal lobe apex: Acute. Petal lobe margin: Entire; slightly undulate. Petal lobe texture and luster, upper surface: Smooth, glabrous; velvety; matte. Petal lobe texture and luster, lower surface: Smooth, glabrous; glossy. Throat texture: Smooth, glabrous. Tube texture: Smooth, glabrous. Color: Petal lobe, when opening and fully opened, upper surface: Close to N45A; venation, close to N45A; color does not change with development. Petal lobe, when opening and fully opened, lower surface: Close to 185A; longitudinal stripes, close to 55A; venation, close to N45A; color does not change with development. Throat: Close to N45A and 23A; proximally, close to 23A; venation, similar to lamina colors. Tube: Distally, close to 53C; proximally, close to 145C.

*Calyx*.—Quantity and arrangement: Five sepals arranged in a single whorl, fused at the base; calyx, star-shaped. Sepal length: About 7.3 mm. Sepal width: About 2 mm. Sepal shape: Lanceolate. Sepal apex: Acuminate. Sepal margin: Entire. Sepal texture, upper and lower surfaces: Smooth, glabrous. Sepal color, upper surface: Distally, close to 145B; proximally, close to 145A. Sepal color, lower surface: Distally, close to 145A; proximally, close to 145B; at the apex and margins, close to N34C.

*Peduncles*.—Length: About 5.2 cm. Diameter: About 2.7 mm. Texture: Smooth, glabrous. Aspect: Upright to outwardly. Color: Close to 146A.

*Pedicels*.—Length: About 1.3 cm. Diameter: About 2 mm. Texture: Smooth, glabrous. Aspect: Upright to outwardly. Color: Close to 145A slightly overlain with close to 172B.

*Reproductive organs*.—Stamens: Quantity and arrangement: Typically five; filaments fused to corolla; anthers, connivent. Anther shape: Lanceolate. Anther size: About 1.8 mm by 9.9 mm. Anther color: Close to 160B. Pollen amount: None observed. Pistils: Quantity: Typically one. Pistil length: About 2.5 cm. Style color: Close to 145D. Stigma shape: Globose. Stigma color: Close to 4C. Ovary color: Close to 145B.

*Seeds and fruits*.—To date, seed and fruit production have not been observed on plants of the new *Mandevilla*.

Disease & pest resistance: To date, plants of the new *Mandevilla* have not been noted to be resistant to pathogens and pests common to *Mandevilla* plants.

Garden performance: Plants of the new *Mandevilla* have been observed to tolerate wind, rain and temperatures ranging from about 4° C. to about 30° C.

It is claimed:

1. A new and distinct *Mandevilla* plant named 'Sunpa 316' as illustrated and described.

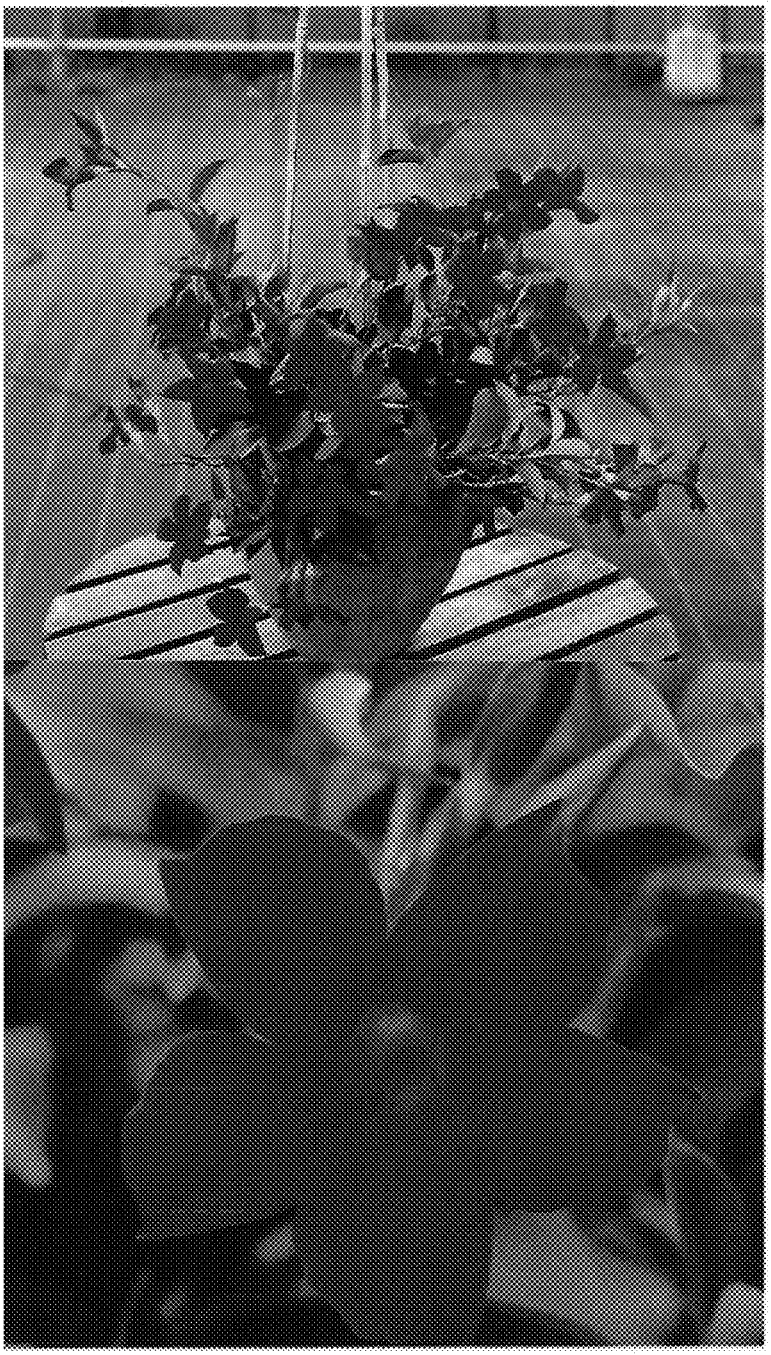

* * * * *